(12) United States Patent
Abraham et al.

(10) Patent No.: US 6,214,879 B1
(45) Date of Patent: Apr. 10, 2001

(54) ALLOSTERIC INHIBITORS OF PYRUVATE KINASE

(75) Inventors: Donald J. Abraham, Midlothian; Richmond E. Danso-Danquah, Richmond; Telih Boyiri, Richmond; Changquing Wang, Richmond; Michael J. Gerber, Richmond, all of VA (US); Stephen J. Hoffman, Englewood, CO (US); Gajanan Joshi, Glen Allen, VA (US)

(73) Assignee: Virginia Commonwealth University, Richmond, VA (US)

( * ) Notice: Subject to any disclaimer, the term of this patent is extended or adjusted under 35 U.S.C. 154(b) by 0 days.

(21) Appl. No.: 09/046,643

(22) Filed: Mar. 24, 1998

(51) Int. Cl.$^7$ ............... A61K 31/185; A61K 31/235; A61K 31/19

(52) U.S. Cl. ............ 514/579; 514/576; 514/544; 514/568

(58) Field of Search ................. 514/544, 568, 514/576, 579

(56) References Cited

U.S. PATENT DOCUMENTS 5,278,168 * 1/1994 Spector et al. .............. 514/279
5,599,974 * 2/1997 Abraham et al. ............. 562/463

OTHER PUBLICATIONS

CA: vol. 76, No. 22396e (Carminatti et al), 1972.*

* cited by examiner

Primary Examiner—Theodore J. Criares
(74) Attorney, Agent, or Firm—McGuireWoods LLP

(57) ABSTRACT

Chemical structures have been identified which allosterically modify pyrvate kinase and either inhibit or activate enzymatic activity. These compounds can be used as pharmaceuticals in the treatment of a wide variety of diseases and disorders where influencing metabolic processes is beneficial, such as the glycolytic pathway, all pathways which use ATP as an energy source, and all pathways which involve 2,3-diphosphoglycerate.

3 Claims, 4 Drawing Sheets

TB-32

TB-88

TB-154

TDD-57

CA-GSJ-2

L-PHENYLATANINE

TB-17

TDD-64

TDD-61

TDD-66

ALLOSTERIC INHIBITORS OF PYRUVATE KINASE

BACKGROUND OF THE INVENTION

1. Field of the Invention

The invention is generally related to pharmaceuticals which are useful for allosterically modifying pyruvate kinase.

2. Description of the Prior Art

Mammalian pyruvate kinase (PK) is a key regulatory glycolytic enzyme that exhibits allosteric kinetic behavior. The basic mechanism of the allosteric regulation of PK at the molecular level is still not known. There are reports that PK undergoes conformational changes and that the changes involve domain events. PK is found in all cells and tissues. It catalyzes the conversion of phospho-enolpyruvate (PEP) and adensosine diphosphate (ADP) into pyruvate and adenosine triphosphate (ATP), as shown in reaction scheme 1.

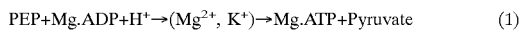

$$\text{PEP} + \text{Mg.ADP} + \text{H}^+ \rightarrow (\text{Mg}^{2+}, \text{K}^+) \rightarrow \text{Mg.ATP} + \text{Pyruvate} \quad (1)$$

The reaction proceeds in two steps. First, the 2-phosphate is removed from PEP to yield ATP and the enolate ion form of pyruvate. The second step involves the protonation and tautomerization of the ion to yield the keto form of pyruvate. The enzyme requires three cation cofactors, two divalent ($Mg^{2+}$ or $Mn^{2+}$) and one monovalent ($K^+$). Positive factors of PK include fructose 1,6 diphosphate, PEP, and low pH. Negative factors of PK include ATP, high pH, and glycogenic amino acids such as alanine and phenylalanine. The products of reaction scheme 1, pyruvate and ATP, are involved in a wide variety of metabolic pathways; therefore, PK can be considered a key enzyme in the glycolytic pathway as well as many other pathways in the cellular metabolism.

In mammals, PK has four isoenzymes which are identified as M-1, M-2, L and R type. The R type PK exists exclusively in red blood cells and its biochemical properties change with cell maturation. Congenital R-PK deficiency in erythrocytes is one of the most frequent enzymopathies involving the glycolytic pathway. It is an autosomal recessive disorder, and in hemozygotes, causes nonspherocytic hemolytic anemia. Heterozygotes do not show symptoms of hemolytic anemia, but have lowered residual PK activity, with increased 2,3-diphosphoglycerate (2,3-DPG) and fairly stable ATP levels. Thus, it appears quite possible that similar results will be obtained pharmacologically from partial inhibition of erythrocyte PK. Because ATP can be synthesized in erythrocytes only by glycolysis, a decreased PK activity causes severe disturbances of the erythrocyte energy metabolism and leads to greatly diminished lifetime of the red blood cells.

SUMMARY OF THE INVENTION

It is an object of this invention to provide pharmaceuticals suitable for allosterically modifying PK.

It is another object of this invention to use a family of pharmaceuticals to regulate the 2,3-DPG and ATP levels in vivo.

It is yet another object of this invention to use a family of pharmaceuticals to regulate the glycolytic pathway in vivo.

According to the invention, a family of compounds has been identified which allosterically modify pyruvate kinase. One group within the family will be useful for the delivery of additional oxygen to tissues by increasing the 2,3-DPG concentration in vivo, and this can be useful in a wide variety of clinical conditions and disease states including radiation oncology, whole body and tissue hypothermia, sepsis, wound healing, diabetic ulcers, pressure sores, tissue transplants, stroke, shock, cardiovascular and angina applications, acute respiratory distress syndrome (ARDS), chronic respiratory insufficiency, pulmonary fibrosis, interstitial lung disease, peripheral vascular disease (e.g., intermittent claudication), ischemia, etc. Another group within the family cause depletion of 2,3-DPG much faster than the control metabolic rate and should be useful in the treatment of sickle cell anemia and other disorders (anticancer therapy, e.g., causing increase in tumor hypoxia thus enhancing hypoxic cell sensitizers such as terapazamine). PK contributes to the establishment of steady-state levels of 2,3-DPG which is important since 2,3-DPG is an allosteric effector of oxygen binding to hemoglobin. PK was found to have an inverse relationship with 2,3-DPG levels in human erythrocytes. An increase in the level of 2,3-DPG induces a rightward shift of the oxygen-hemoglobin dissociation curve, indicating that the quaternary conformational equilibrium of hemoglobin is perturbed toward the T, or deoxygenated state. In other words, oxygen is more quickly being delivered from blood to tissues. Similarly, a decrease in the level of 2,3-DPG concentration induces a leftward shift of the oxygen-hemoglobin dissociation curve and shifts the allosteric equilibribrium to the R, or oxygenated state. Such agents will be useful as antisickling agents. Increasing erythrocyte 2,3-DPG concentrations through the intervention of PK inhibition will find use in many clinical settings where more delivery of tissue oxygenation is desired. The activators of PK will also be useful as antisickling agents since they would produce a therapeutic inhibition of the intracellular polymerization that underlies sickling by increasing oxygen affinity due to the 2,3-DPG depletion, thereby stabilizing the more soluble oxy-hemoglobin. In addition, as discussed above, the activators can also be used in anticancer treatments.

BRIEF DESCRIPTION OF THE DRAWINGS

The foregoing and other objects, aspects and advantages will be better understood from the following detailed description of the preferred embodiments of the invention with reference to the drawings, in which.

DETAILED DESCRIPTION OF THE PREFERRED EMBODIMENTS OF THE INVENTION

Figure 3A:
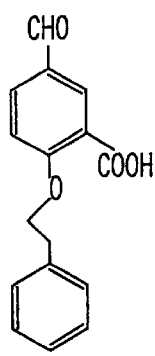
FIGS. 3a–3r are chemical structures of various allosteric inhibitors and activators of PK activity. Structures in FIGS. 3a–3f are allosteric inhibitors with the phenylalanine of FIG. 3f being the control. Structures in FIGS. 3g–r are allosteric activators.

A family of compounds have been identified which allosterically modify pyruvate kinase. One group within the family are allosteric inhibitors, while another group within the family are allosteric activators. FIGS. 3a–r show the chemical structures of the compounds tested within the family and Example 3 describes the synthesis of these compounds. Example 1 explains how the PK was isolated and purified, and Example 2 discusses the test procedures used. Table 1 shows the effect of various allosteric inhibitors on PK activity and Table 2 shows the effect of various allosteric activators on PK activity.

TABLE 1

| Compound Name | Concentration (mM) | % PK Inhibition |
| --- | --- | --- |
| L-Phenylalanine | 10 | 15 |
| L-Phenylalanine | 30 | 72 |
| TB 32 | 0.5 | 48 |
| TB 32 | 2 | 77 |
| TB 32 | 3 | 80 |
| TB 88 | 0.5 | 16 |
| TB 88 | 2.5 | 28 |
| TB 154 | 0.5 | 19 |
| TB 154 | 2 | 28 |
| TDD 57 | 0.5 | 36 |
| CA-GSJ-2 | 0.5 | 36 |

TABLE 2

| Compound Name | Concentration (mM) | % PK activation |
| --- | --- | --- |
| TB 120 | 1 | 17 |
| TB 595 | 1 | 33 |
| TB 159 | 0.25 | 13 |
| TB 17 | 1 | 21 |
| TDD 64 | 1 | 24 |
| TDD 61 | 1 | 47 |
| TDD 66 | 0.5 | 31 |
| CA-GSJ-3 | 1 | 12 |
| INN 261 | 0.25 | 2 |
| RSR 13 | 1 | 13 |
| JP7 | 1 | 14 |
| TB562 | 1 | 12 |

As can be seen from Table 1, TB 32 can have the same or greater inhibitory effect on PK as phenylalinine at an order of magnitude less concentration. Hence TB 32 is one of the most potent inhibitors of PK discovered to date. Furthermore, the remaining data in Table 1 shows that the other compounds within the family contemplated by this invention are significantly more potent inhibitors of PK then phenylalanine.

Table 2 shows that a wide variety of compounds, at low concentrations, can be used to significantly increase PK activation.

Derivatives of the compounds can be made which will also exhibit the same or enhanced allosteric effects on PK. These derivatives might advantageously be formed at the carboxylic acid moiety (by replacement of the hydrogen), but may also be configured at the aldehyde or be ionic in nature. These derivatives can include the substitution of salt or metal cations for hydrogen groups, such as sodium, potassium, lithium, ammonium, and alkali and alkaline metals (Mn and Mg, etc), or the formation of ester or ether derivatives at the hydrogen groups such as $C_{1-12}$ alkyl groups, or involve similar substitutions.

This invention contemplates the use of the allosteric modifiers of PK to treat a wide variety of disorders by influencing metabolic pathways such as the glycolytic pathway, pathways which use ATP as an energy source, and pathways affected by 2,3-DPG. For exemplary purposes only, the compounds may be used in the following clinical settings: radiation oncology, transplantation, hypothermia (whole body and tissue), resuscitation from hemorrhagic shock, wound healing, tissue transplation, treatment of diabetic ulcers and chronic leg ulcers, stroke, during bypass surgery, ischemia, cardiovascular/angina applications, Alzheimer's disease, ARDS, chronic respiratory insufficiency, pulmonary fibrosis, interstitial lung disease, chronic obstructive pulmonary disease, peripheral vascular disease (e.g., intermittent claudication), sepsis, anticancer therapy, sickle cell anemia, etc. The compounds might also be used to counteract aging of stored blood by impacting the rate of release of 2,3-DPG from the blood. The allosteric modifier compounds can be added directly to whole blood or packed cells extra corporally or be provided to the patient directly by i.p., i.v., i.m., oral, inhalation (aerosolized delivery), transdermal, sublingual and other delivery routes. Appropriate pharmaceutical preparations can include liquid and solid materials in the preparation of injectable or orally administered (tablets and capsules) or other delivery routes. Examples of solid diluents and excipients include lactose starch, disintegrating agents, and coatings. Buffers (preferably which render the composition isotonic), carrier fluids (including water, oils, etc.), surfactants (Tween, oleic acid, sorbitan trioleate, etc.), preservatives (parabens, benzalkonium chloride, EDTA, etc.), and the like may all be combined with one or more (combinations of compounds being specifically contemplated herein) PK allosteric modifiers to produce a pharmaceutically acceptable (stable, safe and efficacious) product which can be delivered to a patient or blood sample to allosterically modify PK. Depending upon the disorder to be treated, an inhibitor or an activator of PK will be chosen for administration. The dose will be a function of the patient (sex, age, etc.), the condition being treated, the route of delivery, and other factors. The dose should be sufficient to either activate or inhibit pyruvate kinase activity (depending on the allosteric modifier chosen (e.g., inhibitor or activator).

EXAMPLE 1

Method of Purification of PK

Human R-PK is usually prepared from whole blood according to the method described in by Kohn et al., *Meth. Enzymol.* 90:131–140. This method uses ammonium sulfate precipitation followed by affinity chromatography with Blue Dextran-Sepharose. A major drawback of this method is the low binding capacity of the resin used with PK under the conditions described (1 ml absorbent per 1 IU or PK). However, in order to prepare large quantities of enzyme, a number of dye-affinity absorbents were tried in our laboratory, and it was discovered that using Red A (Amicon) works well under optimized conditions. For exemplary purposes only, the detailed procedures for using Red A column are discussed below.

Purification of Pyruvate Kinase from human whole blood:

Human whole blood required to isolate the enzyme was obtained from the Medical College of Virginia's Blood bank. All purification steps were carried out at 4° C. ADP, PEP, NADH, LDH, and all buffer salts were obtained from Sigma Chemicals, Inc. All buffers contain 10% (V/V) glycerol, 2 mM β mercaptoethanol (β-ME), 10 mM EDTA, 10 mM 4-aminocaproic acid (ACA), and 1 mM phenylmethanesulfonylfluoride (PMSF). The following three buffers were used during the isolation and purification of the enzymes from whole blood.

Buffers:

A: 10 mM TRIS, 80 mM ME, pH 7.5

B: 10 mM TRIS, 800 mM KCl, 1 mM ME, 0.5 mM $MgSO_4$, pH 7.5

C: 20 mM TRIS, 800 mM KCl, 1 mM ME, 1 mM EDTA, 1 mM FDP, pH 7.5

The four units of human whole blood obtained from the Blood Bank were mixed with 2 vol. gelatin solution (10 mg/ml heparin) and 1 vol. 145 mM NaCl, centrifuged at 4000 g for 15 min., and the residual buffy coat was eliminated. The washed red cells were mixed with 2 vol. $H_2O$ containing 2 mM ME, 10 mM EDTA, 10 mM ACA, 2 mM PMSF and 10% cold toluene, homogenized for 1 min with a blender homogenizer, and centrifuiged for 30 min at 10,000 g. The upper layer (fat containing) was discarded and the hemolysate was decanted into a beaker. Under gentle agitation, solid $(NH_4)_2SO_4$ (23 g/100 ml) was slowly added into the hemolysate, and the mixture was incubated at 4° C. for 2 hrs. The precipitate was collected by centrifugation at 10,000 g for 30 min. The pellets were collected and dissolved by adding 11 g/100 ml $(NH_4)_2SO_4$ adjusted to pH 8.0 with solid TRIS, centrifuged, and the supernatant was then collected while discarding the residual pellets. To this supernatant was then added solid $(NH_4)_2SO_4$ to get 22 g/100 ml final concentration. The pH was adjusted to 6.6 with 10% acetic acid and the solution was centrifuged at 10,000 g for 30 min to collect the precipitate. The precipitate was washed one more time with 21 g/100 ml $(NH_4)_2SO_4$, pH 6.6, and centrifuged to collect the pellets. The pellets were then dissolved in buffer A, centrifuged at 26,000 g for 30 min to collect the clear supernatant. The total protein and PK concentrations were measured at an optical density of 280 nm and 340 nm, respectively.

The crude isolated PK (100 ml of 3 mg/ml sample containing about 1 mg PK) was then loaded onto a Amicon Red A column (5×35 cm) equilibrated with Buffer A. The column was washed with 500 ml Buffer A, then with Buffer B until absorbency at 280 nm disappeared with no detectable PK activity in the flow through. The enzyme was eluted with 1.5 L Buffer C with a flow rate of 2–5 ml/min, by collecting into all 10 ml fractions. The PK activity of each fraction was then measured and all active fractions were pooled together. The pooled fractions were concentrated into a final vol. of 15–25 ml with an Amicon ultrafiltration concentrator. All concentrated enzyme fractions were then transferred into a dialysis membrane bag and dialyzed against 3×300 ml Buffer A. The PK can also be precipitated by dialyzing against 50 mM TRIS, pH 7.5 containing 35 g/100 ml $(NH_4)_2SO_4$. Pellets should be stored under −70° C. The overall yeild of the enzyme isolation and purification using this process is 0.5–1.0 mg.

The purity of the preparation was assessed by SDS-PAGE. A typical result of the preparation shows three major bands around 62, 58 and 54 kD. The result is largely consistent with the reported values. The three bands are estimated to be larger than 90% of the total proteins.

EXAMPLE 2

Measurement of PK Activity

Figure 1:
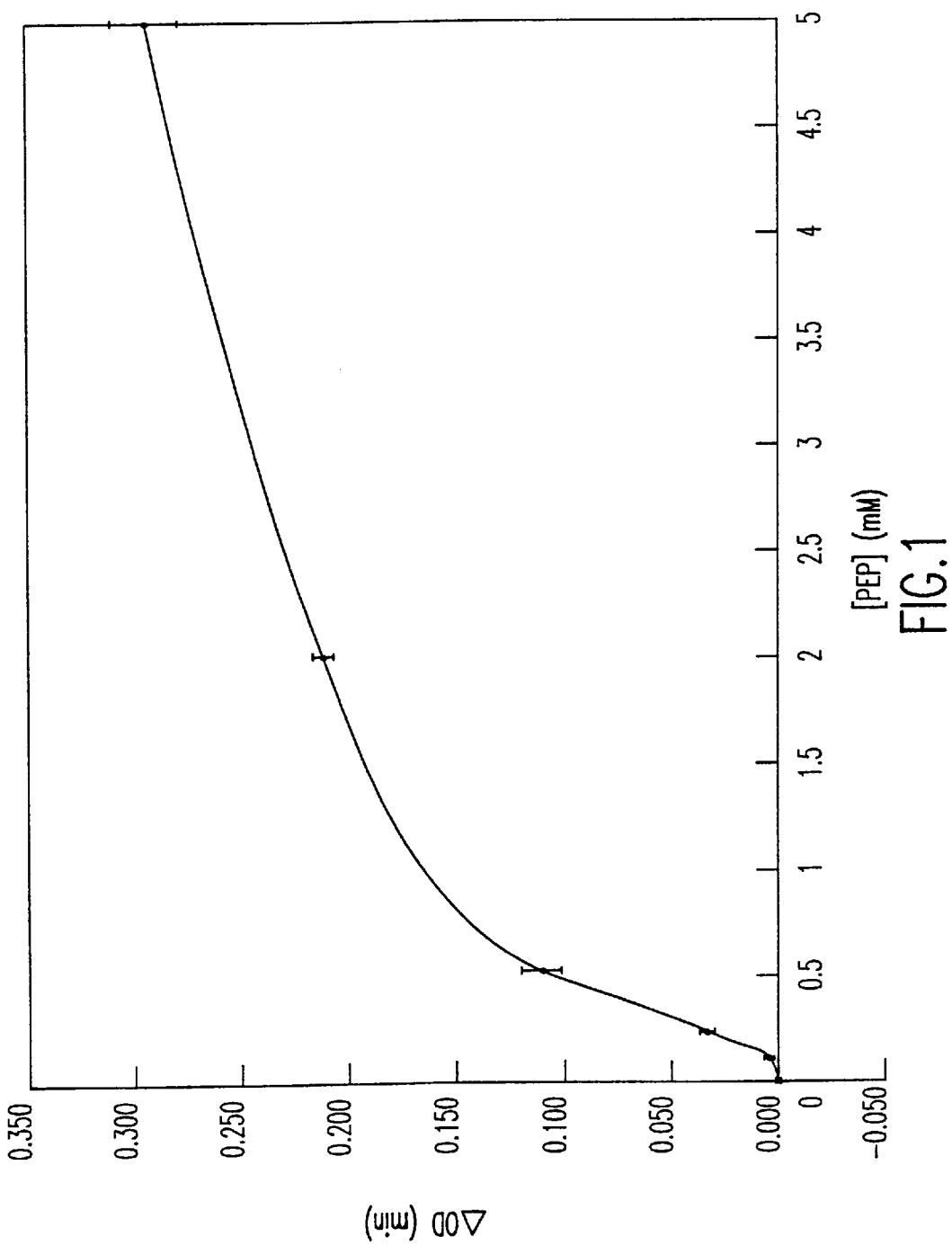
FIG. 1 is a saturation plot as discussed in Example 2 where optical density is measured against various concentrations of PEP. It can be seen that the saturation point is reached when the change in optical density/min is approximately 0.3. In all experiments with the allosteric compounds identified herein, the saturation point was reached prior to addition of the allosteric compound.

PK activity was measured using the assay conditions that are recommended by the International Committee for Standardization in Hematology (ICSH). FIG. 1 shows the saturation curve of PK with respect to PEP. The positive cooperativity of substrate binding is clearly seen from the upward curvature in the Lineweaver plot. The experimental data were fit to the Hill equation. The derived parameters were $K_{0.5S}$=2.37 mM and Hill coefficient ($n_H$) of 1.41.

Figure 2:
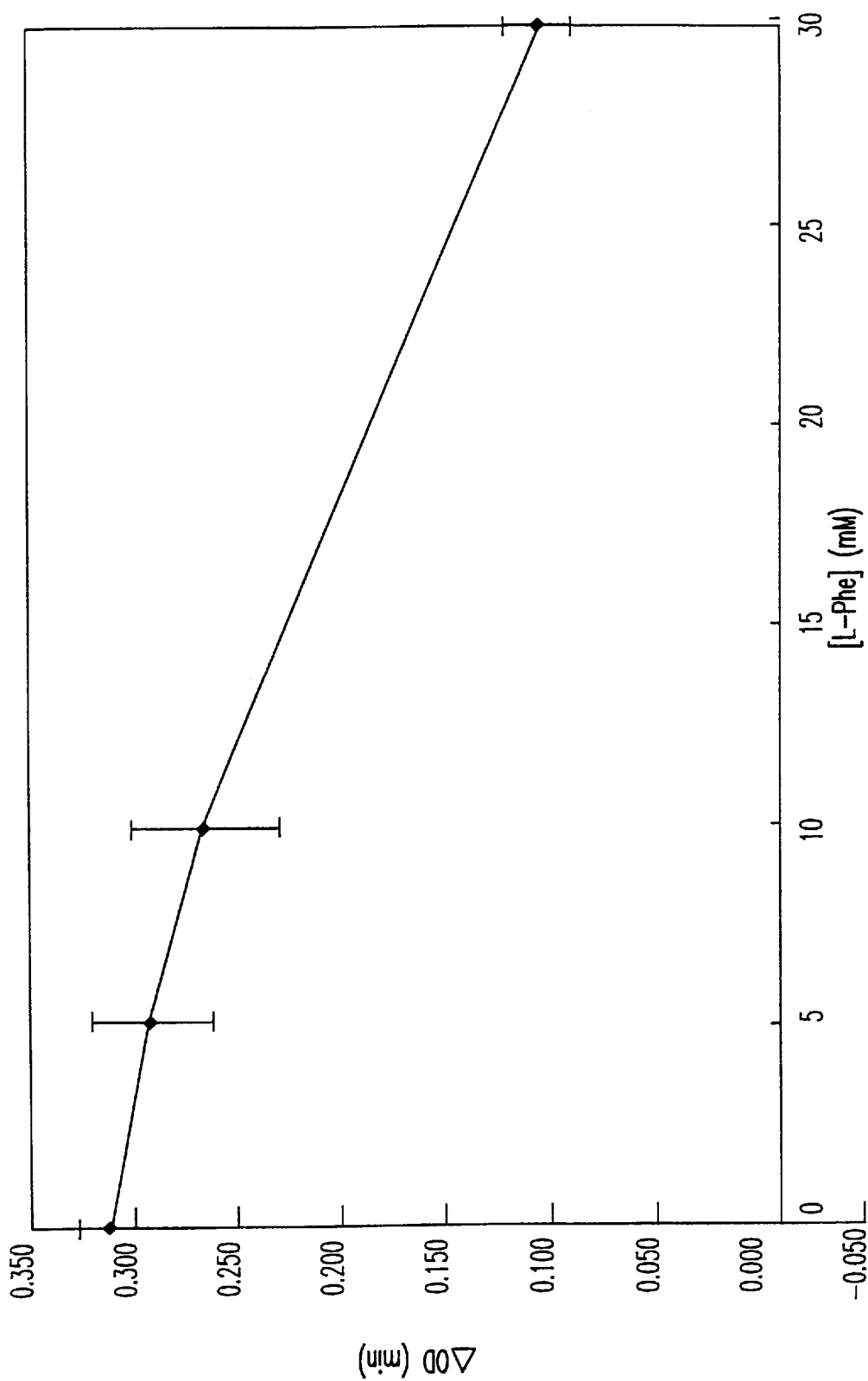
FIG. 2 is a plot of varying concentrations of phenylalanine versus optical density measurements. As discussed in Example 2, phenylalanine is an inhibitor of PK. The decline in optical density shown in FIG. 2 shows that increasing concentrations of phenylalanine result in increasing inhibition of the PK enzyme.

Phenlyalanine has long been known as an allosteric inhibitor of PK. FIG. 2 shows the PK activity measured in the presence of four different concentrations of phenlyalanine. It can be seen from FIG. 2 that an increase in the concentration of phenlyalanine results in a decreased affinity and a more pronounced sigmoidity of the substrate binding. When phenylalanine increases from 0 to 30 mM, the $K_{0.5S}$ increases by 2.5 folds and $n_H$ increases by 1.4 folds, respectively. To avoid fluctuations in measurement of PK parameters, all experiments reported herein and assays were performed using the same batch of preparation and under identical conditions.

Measurement of PK activity of human erythrocyte pyruvate kinase (R-PK):

PK activity is measured by coupling it with lactate dehydrogenase which transforms pyruvate into lactate and oxidizes NADH into NAD. A reduction of oxidation of NADH is followed at 340 nm using the 96 well plate in a Spectramax spectrophotometer (Molecular Devices, Ca.).

The assay buffer (100 mM Tris pH 7.5) was prepared by dissolving TRIS 100 mM, KCl 100 mM, EDTA 0.5 mM, and 10 mM $MgCl_2$ in deionized water. The pH of the solution was adjusted to 7.5 by adding a small amount of TRIS. The stock solution of NADH (20mM), ADP 100 mM (neutralized), LDH 500 IU/ml and PEP 100 mM were prepared in the assay buffer. The following quantities of reagents were added to make 1 ml of assay solution.

| Final Concentration | | |
|---|---|---|
| Assay Buffer | 910 µl | |
| NADH | 10 µl | 0.2 mM |
| ADP | 15 µl | 1.5 mM |
| LDH | 2 µl | 1 IU |
| PK | 10 µl | |

The contents were mixed and incubated for five minutes at 37° C. Then, 50 µl of PEP was added and the absorbance changes were followed at 340 nm. The initial reaction velocity in AU/min was then calculated.

The incubation of human erythrocyte PK with various allosteric modulators in the assay buffer (pH 7.5) or in DMSO solution at different concentrations and at 37° C. resulted in a concentration dependent inhibition or activation of the enzyme. The phenylalanine was used as a standard reference for the inhibition activity assay, and results are presented in FIG. 2 and Table 1. The control samples in each experiment were incubated under the same conditions as without any compound. In all cases, the experiments were begun after saturation with PEP. The percent inhibition of PK activity was calculated by subtracting the activity of the control sample from the activity in the presence of compound. The activity data for various compounds are presented in Tables 1 and 2 where Table 1 shows compounds which demonstrate allosteric inhibition of PK and Table 2 shows the data for allosteric activation of PK.

EXAMPLE 3

TB 32

2-phenylethyloxy-5-formylbenzoic acid, identified as TB 32, is shown in FIG. 3a. The synthesis of this compound is described in detail in U.S. Pat. No. 5,599,974, which is herein incorporated by reference. Methyl-2-hydroxy-5-acetalbenzoate (1.0 g, 4.46 mmol), 2-phenylethylbromide (0.98 g, 5.27 mmol) and powdered potassium carbonate (2.0 g, 14.5 mmol) in dry acetone were heated to reflux for twelve hours. The reaction mixture was filtered while hot and the solvent was removed under vacuum. The crude product was flash chromatographed using hexane-ethyl acetate mixtures and the desired intermediate, methyl-2-phenylethyloxy-5-acetalbenzoate in 10% potassium hydroxide (20 ml) was heated to reflux for 1 hr. The reaction mixture was filtered, cooled and acidified with concentrated hydrochloric acid. The precipitate was filtered, washed thoroughly with water (40 ml), re-dissolved in hot aqueous solution of sodium bicarbonate and extracted with diethyl ether (2×20 ml). The aqueous layer was acidified, the product filtered, washed with small amounts of diethyl ether, and air dried. Yield 80%; mp 112–114° C.; $^1$H NMR (DMSO-$d_6$) δ 13.05 (s, 1H, $CO_2H$), 9.92 (s, 1H, CHO), 8.19 (d, 1H, ArH), 8.01 (dd, 1H, ArH), 7.2–7.45 (m, 6H, ArH), 4.35 (t, 2H, $CH_2$) 3.05 (t, 2H, $CH_2$); Anal. Calcd. for ($C_{16}H_{12}O_4$. 0.25 $H_2O$) C, 69.94, H, 5.32, found C, 70.29, H, 5.28.

TB 88

Figure 3B:
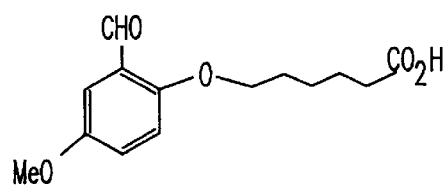

6-(2-formyl-4-methoxyphenoxy)hexanoic acid, identified as TB 88, is shown in FIG. 3b. 2-hydroxy-5-methoxybenzaldehyde (1.52 g, 10 mmol), methyl 6-bromohexanoate (2.08 g, 10 mmol), and anhydrous potassium carbonate (2.0 g, 14.5 mmol) were stirred in anhydrous DMF (50 mL) at 60° C. for 24 hours. The reaction mixture was filtered and the filtrate diluted with 50 mL ethyl acetate, washed twice with 200 mL water, dried over anhydrous $Na_2SO_4$ and evaporated to dryness under reduced pressure. The intermediate solid ester (2.80 g, 10 mmol) was hydrolyzed by stirring it in the presence of 10% potassium hydroxide (2/1: water/ethanol) at room temperature for 2 hours (i.e., stage 2A). The ethanol was removed under reduced pressure and the basic aqueous phase extracted with ethyl acetate. The desired aldehyde acid was precipitated from the alkaline solution by acidification and the precipitate filtered, washed with copious amounts of water and oven dried at 70° C. 2.61 g (98% yield; m.p. 104–106° C.) of 6-(2-formyl-4-methoxyphenoxy)hexanoic acid product, designated as compound TB88, was obtained with the structure of the product confirmed by NMR and IR spectroscopy and elemental analysis.

Compounds TB154, TB 120 and TB159 were prepared from the corresponding starting materials, hydroxy-substituted benzladehyde and methyl bromohexanoate, by following the procedure described herein for TB88.

TB 154

Figure 3C:
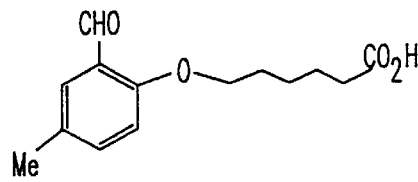
Figure 3D:
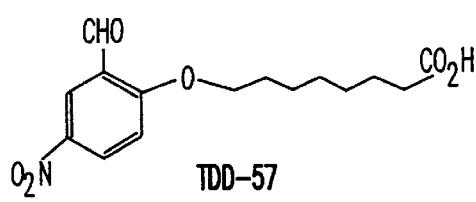
Figure 3E:
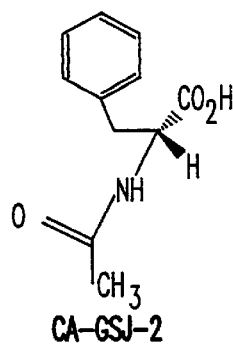
Figure 3F:
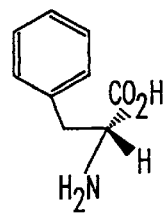
Figure 3G:
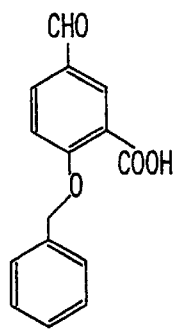
Figure 3H:
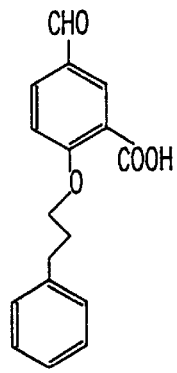
Figure 3I:
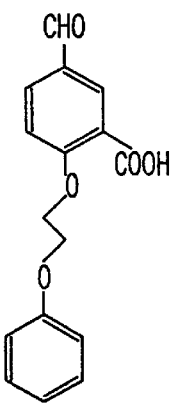
Figure 3J:
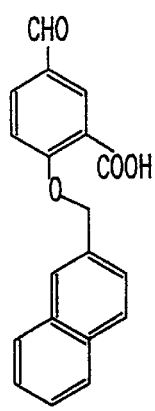

6-(2-formyl-4-methylphenoxy)hexanoic acid, identified as TB 154 and shown in FIG. 3c was synthesized using 2-hydrocy-5-methylbenzaldehyde (1.36 g, 10 mmol) and methyl 6-bromohexanoate (2.08 g, 10 mmol) as starting materials with a yield of 2.33 g (93%). The compound melted at 97–99° C. and its structure was confirmed by NMR. Anal. Calcd for $C_{14}H18O_4$: C, 67.17, H, 7.26. Found C, 67.27;H, 7.24.

TDD 57

6-(2-formyl-4-nitrophenoxy)octanoic Acid, identified as TDD-57 was prepared as follows: 2-Hydroxy-5-nitrobenzaldehyde (1.67 g, 10 mmol), methyl 8-bromooctanate (2.64 g. 12 mmol), and anhydrous potassium carbonate in anhydrous acetonitrile (40 mL) were stirred at 70° C. under nitrogen overnight. The cooled reaction mixture was diluted with ethyl acetate (60 mL) and washed with water (2×30 mL), brine (30 mL), dried ($MgSO_4$) and evaporated to dryness under reduced pressure. To the intermediate ester (1.4 g, 4.3 mmol) in ethanol (30 mL) was added 10% sodium hydroxide (10 mL) and stirred at room temperature for 4 hr. The ethanol was removed under reduced pressure, the aqueous phase diluted with water (50 mL) and extracted with ethyl acetate (2×40 mL). The aqueous phase was acidified with dilute hydrochloric acid, the product extracted with ethyl acetate (3×40 mL), the organic phase washed with brine (30 mL), dried ($MgSO_4$) and evaporated to dryness under reduced pressure to give 1.2 g (90%) of the titled compound. Melting point 102–103° C. The structure of the product was confirmed by NMR. Anal. Calcd. for $C_{15}H_{19}NO_6$: C, 58.25; H, 6.19; N, 4.53; Found: C, 58.04; H, 6.33; N, 4.38.

TB 120

Figure 3K:
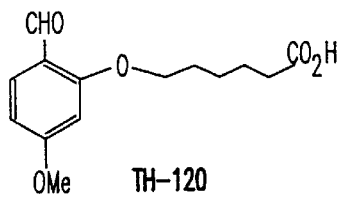

6-(2-formyl-5-methoxyphenoxy)hexanoic acid, designated as compound TB120 and shown in FIG. 3k, was prepared from 2-hydroxy-4-methoxybenzaldehyde (1.52 g, 10 mmol) and methyl 6-bromohexanoate (2.09 g, 10 mmol) as starting materials with a yield of 2.63 g (98.75%) and m.p. of 100–101° C. The structure of the product was confirmed by NMR analysis. Anal. Calcd. for $C_{14}H_{18}O_5$: C, 63.14; H, 6.83. Found: C, 63.23; H, 6.84.

TB 595

Figure 3L:
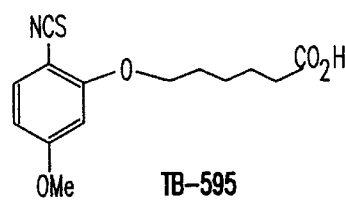
Figure 3O:
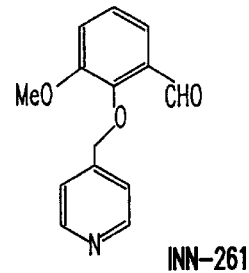

6-(2-isothiocyanoto-5-methoxphenoxy)hexanoic acid, represented as TB595 and shown in FIG. 3L was prepared by a number of steps. The first step involves the reaction of 2-nitro-5-methoxyphenol (1.69 g, 10 mmol) with methyl 6-bromohexanoate (2.08 g, 10 mmol) in dry dimethylformamide and anhydrous potassium carbonate (2.0 g, 14.5 mmol) at 60° C. for 12 hours to produce the intermediate ester, methyl 6-(2-nitro-5-methoxyphenoxy)hexanoate. Hydrogenation of methyl 6-(2-nitro-5-methoxyphenoxy) hexanoate using palladium-on-carbon as catalyst afforded the isolation of methyl 6-(2-amino-5-methoxyphenoxy) hexanoate which was saponified in 10% water/ethanol (1:1) solution of potassium hydroxide to give 6-(2-amino-5-methoxyphenoxy)hexanoic acid in 95% yield. Finally, the reaction of 6-(2-amino-5-methoxyphenoxy)hexanoic acid (1.0 g, 3.9 mmol), thiophosgene (0.8 ml, 4.2 mmol), and pyridine (1.0 g, 7 mmol) in tetrahydrofuran at room temperature gave 0.9 g (78% yield) of the desired product as a colorless powder. The structure of the product was confirmed by NMR. Anal. Calcd for $C_{14}H_{17}NO_4S$: C, 56.92; N, 4.74; S, 10.86.

Found: C, 57.00; H, 5.81; N, 4.76; S, 10.96.

TB 159

Figure 3M:
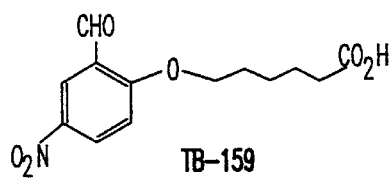
Figure 3N:
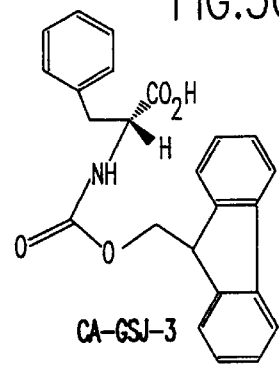

6-(2-formyl-4-nitrophenoxy)hexanoic acid, identified as TB 159 and shown in FIG. 3M was prepared from 2-hydroxy-5-nitrobenzaldehyde (1.67 g, 10 mmol) and methyl 6-bromohexanoate (2.09 g, 10 mmol) as starting materials with a yield of 2.74 g (98%) and a melting point of 121–123° C. The structure of the product was confirmed by NMR. Anal. Calcd for $C_{13}H_{15}NO_6$: C, 55.50; H, 5.39; N, 4.98. Found: C, 55.48; H, 5.40; N, 4.90.

TB 17

2-benzyloxy-5-formylbenzoic acid, identified as TB 17, is shown in FIG. 3g. The synthesis of this compound is described in detail in U.S. Pat. No. 5,599,974 which is incorporated by reference. Methyl-2-hydroxy-5-acetalbenzoate (1.0 g, 4.46 mmol), benzyl bromide (0.76 g, 4.46 mmol) and powdered potassium carbonate (3.0 g, 14.5 mmol) in dry acetone were heated to reflux for 12 hours. The reaction mixture was filtered while hot and the solvent was removed under vacuum. The crude product was flash chromatographed using hexane-ethyl acetate mixtures and the desired intermediate, methyl-2-benzyloxy-5-acetal benzoate, was obtained as a colorless solid. Methyl-2-benzyloxy-5-acetalbenzoate in 10% aqueous potassium hydroxide (20 ml) was heated to reflux for 1 hr. The reaction mixture was filtered, cooled, and acidified with concentrated hydrochloric acid. The precipitate was filtered, washed thoroughly with water (40 ml), redissolved in hot aqueous solution of sodium bicarbonate and extracted with diethyl ether (2×20 ml). The aqueous layer was acidified, the product filtered, washes with small amounts of diethyl ether and air dried. Yield 88%; mp 105–107° C.; $^1$H NMR (DMSO-d$_6$) δ 9.91 (s, 1H, CHO), 7.2–8.6 (m, 8H, ArH), 5.35 (s, 2H, CH$_2$); Anal. Calcd. for (C$_{15}$H$_{12}$O$_4$) C, 70.34; H, 4.72; found C, 70.17; H 4.99.

TDD 64

2-phenylpropyloxy-5-formylbenzoic acid, identified as TDD-64 and shown in FIG. 3h was prepared as follows: Methyl-2-hydroxy-5-acetalbenzoate (900 mg, 5 mmol), 1-bromo-3-phenylpropane (1.5 g, 7.5 mmol), anhydrous potassium carbonate (1.4 g, 10 mmol) in dimethylformamide (20 mL) were stirred at 80° C. under nitrogen overnight. The cooled reaction mixture was diluted with ethyl acetate (100 mL) and washed with water (3×40 mL), brine (40 mL), dried (MgSO$_4$) and evaporated to dryness under reduced pressure. The product was purified by flash chromatography on silica gel eluting with hexane-ethyl acetate mixture (3:1). To the intermediate ester (1.5 g, 5 mmol) in ethanol (40 mL) was added lithium hydroxide (181 mg, 7.5 mmol) in water (20 mL) and stirred at room temperature for 4 hr. The ethanol was removed under reduced pressure, the aqueous phase diluted with water (100 mL) and extracted with ethyl acetate (2×40 mL). the aqueous phase was acidified with dilute hydrochloric acid, the product extracted with ethyl acetate (3×40 mL) the organic phase washed with brine (40 mL), dried (MgSO$_4$) and evaporated to dryness under reduced pressure. Flash chromatography on silica gel eluting with hexane-ethyl acetate mixture (1:1) gave 1.2 g (86%) of the titled compound with a melting point of 91–92° C. The structure of the product was confirmed by NMR. Anal. Calcd. for C$_{17}$H$_{16}$O$_4$: C, 71.82; H, 5.67.

Found: C, 71.86; H, 5.70.

TDD 61

2-phenoxypropyloxy-5-formylbenzoic Acid, identified as TDD-61 was prepared as follows: Methyl-2-hydroxy-5-acetalbenzoate (900 mg, 5 mmol), 3-phenoxypropyl bromide (2.15 g, 10 mmol), anhydrous potassium carbonate (1.4 g, 10 mmol) in dimethylformamide (20 mL) were stirred at 80° C. under nitrogen overnight. The cooled reaction mixture was diluted with ethyl acetate (100 mL) and washed with water (3×40 mL), brine (40 mL), dried (MgSO$_4$) and evaporated to dryness under reduced pressure. The product was purified by flash chromatography on silica gel eluting with hexane-ethyl acetate mixture (3:1). To the intermediate ester (1.8 g, 5.7 mmol) in ethanol (30 mL) was added lithium hydroxide (272 mg, 11.3 mmol) in water (10 mL) and stirred at room temperature for 4 hr. The ethanol was removed under reduced pressure, the aqueous phase diluted with water (100 mL) and extracted with ethyl acetate (2×40 mL). The aqueous phase was acidified with dilute hydrochloric acid, the product extracted with ethyl acetate (3×40 mL), the organic phase washed with brine (40 mL), dried (MgSO$_4$) and evaporated to dryness under reduced pressure. Flash chromatography on silica gel eluting the hexane-ethyl acetate mixture (1:1) gave 1.5 g (88%) of the titled compound. Melting point, 110–111° C. The structure of the product was confirmed by NMR. Anal. Calcd. for C$_{17}$H$_{16}$O$_5$: C, 67.99; H, 5.37. Found: C, 68.00; H, 5.37.

TDD 66

2-naphthylmethyloxy-5-formylbenzoic Acid, identified as TDD-66 and shown in FIG. 3j was prepared as follows: Methyl-2-hydroxy-5-acetalbenzoate (900 mg, 5 mnol), 2-(bromomethyl)naphthalene (1.66 g, 7.5 mmol), anhydrous potassium carbonate (1.4 g, 10 mmol) in dimethylformamide (20 mL) were stirred at 80° C. under nitrogen overnight. The cooled reaction mixture was diluted with ethyl acetate (100 mL) and washed with water (3×40 mL), brine (40 mL), dried (MgSO$_4$) and evaporated to dryness under reduced pressure. The product was purified by flash chromatography on silica gel eluting with hexane-ethyl acetate mixture (3:1). To the intermediate ester (1.5 g, 4.9 mmol) in ethanol (40 mL) was added lithium hydroxide (169 mg, 1.5 mmol) in water (20 mL) and stirred at room temperature for 4 hr. The ethanol was removed under reduced pressure, the aqueous phase diluted with water (100 mL) and extracted with ethyl acetate (2×40 mL). The aqueous phase was acidified with dilute hydrochloric acid, the product extracted with ethyl acetate (3×40 mL) the organic phase washed with brine (40 mL), dried (MgSO$_4$) and evaporated to dryness under reduced pressure. Flash chromatography on silica gel eluting with hexane-ethyl acetate mixture (1:1) gave 1.3 g (93%) of the titled compound with a melting point, 161–162° C. The structure of the product was confirmed by NMR. Anal. Calcd. for C$_{19}$H$_{14}$O$_4$: C, 74.50; H, 4.61.

Found: C, 74.25; H, 4.70.

INN261

3-methyl-4-(3-pyridinylmethoxy)benzaldehyde, referred to as INN 261 and shown in FIG. 3o. A mixture orthovanillin (3.04 g, 20 mmol), 4-chloromethylpyridinium hydrochloride (3.28 g, 20 mmol), potassium carbonate (8.29 g, 60 mmol) and potassium iodide (0.4 g) in dry dimethylformamide (35 mL) was stirred at 80–90° C. for approximately 13 hours. The mixture was allowed to cool, diluted with ethyl acetate (100 mL) and washed with water (3×100 mL). The ethyl acetate layer was washed with water, brine, dried over MgSO$_4$, filtered and evaporated to dryness under reduced pressure to give an impure brownish solid. This product was purified by recrystallization from ether-hexane mixtures to give 2.84 g (58% yield) of brown needle-like crystals. The structure of the product was confirmed by NMR. Anal. Calcd. for C$_{14}$, H$_{13}$, NO$_3$: C, 69:12; H, 5:39; N, 5.76. Found: C, 69:27; H, 5.45; N, 5.70.

RSR 13

Figure 3P:
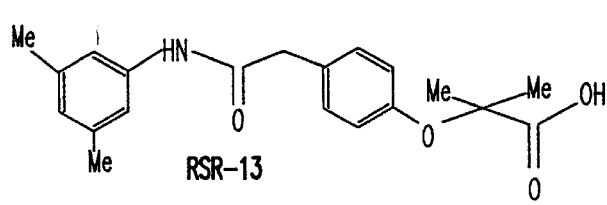
Figure 3R:
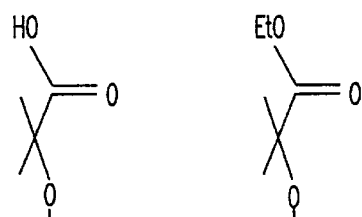

2-[4-((((3,5-dimethyl-phenyl)amino)carbonyl)methyl)phenoxy]-2-methyl propionic acid, identified as RSR 13, is shown in FIG. 3p. The synthesis of this compound is discussed in detail in U.S. Pat. Nos. 5,290,803, 5,432,19, and 5,122,539, each of which is herein incorporated by reference. 3.26 g (21 mmol) of 4-hydroxyphenylacetic acid (HPAA), 5.3 ml (42 mmol) of 3,5 dimethyl aniline, and 25 ml of xylene is heated to reflux. The reaction mixture is cooled, washed with dilute HCl, water and brine and extracted with aqueous NaOH. The combined alkali layer is washed with ether, cooled and acidified to produce the intermediate product N-(3,5-dimethylphenyl)-4-hydroxybenzylamide. 1.27 g (5 mmol) of the intermediate is used to produce RSR-13 by recrystallization from acetone and petroleum ether and O-alkylation (68% yield; mp 85° C.). Alternatively, the procedures of German Patent Application 2,432,560 may also be used.

JP 7

Figure 3Q:
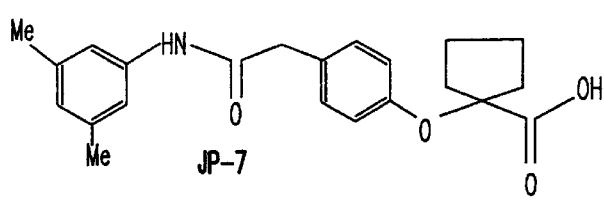

1-[4-((((3,5 -dichlorophenyl)amino)carbonyl)methyl)phenoxy] cyclopentanecarboxylic acid (C$_{19}$H$_{17}$NO$_4$Cl$_2$), identified as JP 7, is shown in FIG. 3q. The synthesis of this compound is described in U.S. Pat. No. 5,432,191 which is herein incorporated by reference. N-(3,5-methylphenyl-4-hydroxyphenylacetamide in THF is treated with NaOH and CHCl$_3$ at −20° C. Cyclopentanone is added dropwise at −20° C. and stirred overnight at room temperature. THF is removed under vacuum and the residue is dissolved in water, followed by acidification with 35% Hcl. The precipitated sold is extracted into ether and treated with 6% sodium bicarbonate solution. The product is obtained from the aqueous layer upon acidification and is purified by repeated extraction into ether and sodium bicarbonate.

TB 562

1-{2-[4-[[aminocarbonyl]methyl]phenoxy]-2-methylpropionic acid}, 1'-{ethyl 2-[4-[[aminocarbonyl] methyl]phenoxy]-2-methylpropionate}-2,2'-diphenoxypropane, designated as TB562 is shown as FIG. 3r. A mixture of 2-nitrophenol (2.78 g, 20 mmol), 1,3-dibromopropane (2.02 g, 10 mmol), anhydrous potassium carbonate (3.0 g, 22 mmol), and acetone (100 ml) was stirred at reflux for 48 hours. The reaction mixture was cooled, filtered, and the solvent removed by reduced pressure to obtain a pale yellow solid as the intermediate 1,1'-dinitro-2,2'-diphenoxypropane (2.83 g, 99% yield). The dinitro intermediate was dissolved in ethanol (100 ml) and hydrogenated using palladium-on-carbon (1.0 g) as the catalyst to afford the isolation of 1,1'-diamino-2,2'-diphenoxypropane (2.52 g, 98% yield). A mixture of 1,1'-diamino2,2'-diphenoxypropane (2.52 g, 9.8 mmol) and 4-hydroxyphenylacetic acid in p-xylene was refluxed for 48 hours and the water was removed from the reaction mixture using the Dean Stark trap. Upon cooling the reaction mixture, the intermediate 1,1'-[4-((diaminocarbonyl)methyl) phenol]-2,2'-diphenoxypropane (4.77 g, 91% yield) precipitated out. This product was filtered, washed with copious amounts of hexane, and dried. The 1,1'-[4' ((diaminocarbonyl)methyl)phenol]-2,2'-diphenoxypropane (4.77 g, 9.1 mmol) was dissolved in anhydrous dimethyl-formamide (40 ml) and reacted with ethyl α-bromoisobutyrate (5.31 g, 27.2 mmol) in the presence of anhydrous potassium carbonate (3.5 g, 25 mmol) at 80° C. for 24 hours to give the diester, 1,1'-[ethyl 2-[4-((aminocarbonyl)methyl)phenoxy]-2-methyl-propionate]-2, 2'-diphenoxypropropane (6.8 g) in 90% yield. The desired half acid-half ester was prepared from the diester as follows: In a 100 ml flask equipped with a magnetic stirrer, reflux condenser and dropping funnel were placed 1,1'-[ethyl 2-[4-((aminocarbonyl)methyl)phenoxy]-2-methyl-propionate]-2, 2'-diphenoxypropane (6.8 g, 9.0 mmol) and absolute ethanol (50 ml). The mixture was heated to reflux and a solution of potassium hydroxide (0.53 g, 9.0 mmol) in ethanol (20 ml) was added. The mixture was refluxed overnighted, cooled and the monopotassium salt that precipitated out was filtered. The precipitate was washed with ethanol (40 ml) and then with hexane and oven dried. Concentration of the mother liqour yielded another crop of crystals which was combined with the first crop, redissolved in water, acidified with dilute hydrochloric acid, the precipitate filtered, washed with copious amounts of water and oven dried to give 70% yield (5.1 g) of the title compound. The structure of the final product was confirmed by NMR. Anal. Calcd for $C_{41}H_{46}N_2O_{10}$: C, 67.74; H, 6.39; N, 3.85. Found: C, 67.73; H, 6.36; N, 3.88.

CA-GSJ-2 and CA-GSJ-3

These compounds, shown in FIGS. 3e and 3n respectively, were purchased from the Aldrich Chemical Company and are commercially available as N-acetyl-L-Phenylalanine and 9-Fluorenylmethoxycarbonyl-L-Phenylalanine, respectively.

While the invention has been described in terms of its preferred embodiments, those siklled in the art will recognize that the invention can be practiced with modification within the spirit and scope of the appended claims.

We claim:

1. A method for allosterically modifying pyruvate kinase in a patient, comprisisng the step of providing a patient in need thereof with sufficient quantity of a compound which iinhibits pyruvate kinase activity, wherein said compound is selected from the group consisting of 2-phenylethyloxy-5-formylbenzoic acid, 6-(2-formyl-4-methoxyphenoxy) hexanoic acid, 6-(2-formyl-4-methylphenoxy)hexanoic acid, 6-(2-formyl-4-nitrophenoxy)octanoic acid, and 2-amino-4-phenylbutyric acid.

2. A method for regulating 2,3-diphosphoglycerate levels in blood comprising the step of adding to blood a sufficient quantity of a compound which inhibits pyruvate kinase activity wherein said compound is selected from the group consisting of 2-phenylethyloxy-5-formylbenzoic acid, 6-(2-formyl-4-methoxyphenoxy)hexanoic acid, 6-(2-formyl-4-methylphenoxy)hexanoic acid, 6-(2-formyl-4-nitrophenoxy)octanoic acid, and 2-amino-4-phenylbutyric acid.

3. A method for regulating the glycolytic pathway in a patient by inhibiting pyruvate kinase activity, comprising the steps of administering to a patient in need thereof a sufficient quantity of a compound which allosterically modifies and inhibits pyruvate kinase, wherein the compound is selected from the group consisting of 2-phenylethyloxy-5-formylbenzoic acid, 6-(2-formyl-4-methoxyphenoxy) hexanoic acid, 6-(2-formyl-4-methylphenoxy)hexanoic acid, 6-(2-formyl-4-nitrophenoxy)octanoic acid, and 2-amino-4-phenylbutyric acid.

* * * * *